(12) United States Patent
Chen (10) Patent No.: US 7,992,562 B2
(45) Date of Patent: Aug. 9, 2011

(54) LARYNGEAL MASK AIRWAY INSTALLATION KIT, LARYNGEAL MASK AIRWAY WITH A STYLET, AND STYLET

(76) Inventor: Tien-Sheng Chen, Taipei (TW)

(*) Notice: Subject to any disclaimer, the term of this patent is extended or adjusted under 35 U.S.C. 154(b) by 928 days.

(21) Appl. No.: 11/934,168

(22) Filed: Nov. 2, 2007

(65) Prior Publication Data

US 2009/0090358 A1  Apr. 9, 2009

(30) Foreign Application Priority Data

Oct. 4, 2007  (TW) .............................. 96216603 U (51) Int. Cl.
*A62B 9/06* (2006.01)
*F24J 3/00* (2006.01)
(52) U.S. Cl. .............................. 128/207.14; 128/200.26
(58) Field of Classification Search ............. 128/200.26, 128/207.14, 207.15
See application file for complete search history.

(56) References Cited

U.S. PATENT DOCUMENTS

| | | | | |
|---|---|---|---|---|
| 4,637,389 A * | 1/1987 | Heyden | ..................... | 128/207.15 |
| 4,840,172 A * | 6/1989 | Augustine et al. | ........ | 128/207.14 |
| 5,038,766 A * | 8/1991 | Parker | ..................... | 128/200.26 |
| 5,241,956 A | 9/1993 | Brain | | |
| 5,758,656 A * | 6/1998 | Schroeder | ..................... | 600/585 |
| 5,829,430 A * | 11/1998 | Islava | ..................... | 128/200.26 |
| 5,896,858 A * | 4/1999 | Brain | ..................... | 128/207.15 |
| 5,937,860 A * | 8/1999 | Cook | ..................... | 128/207.15 |
| 6,164,277 A * | 12/2000 | Merideth | ................. | 128/207.14 |
| 6,439,232 B1 * | 8/2002 | Brain | ..................... | 128/207.15 |
| 7,552,729 B2 * | 6/2009 | O'Mara | ................... | 128/200.26 |
| 2004/0215061 A1 * | 10/2004 | Kimmel et al. | ............... | 600/179 |

* cited by examiner

*Primary Examiner* — Justine R Yu
*Assistant Examiner* — Si Lee
(74) *Attorney, Agent, or Firm* — Alan Kamrath; Kamrath & Associates PA (57) ABSTRACT

A laryngeal mask airway installation kit includes a laryngeal mask airway having a gastric access tube and includes a stylet capable of being inserted into the gastric access tube from the inlet end. When bent, the stylet changes the original shape of the laryngeal mask airway, thus facilitating the installation of the laryngeal mask airway.

9 Claims, 12 Drawing Sheets

LARYNGEAL MASK AIRWAY INSTALLATION KIT, LARYNGEAL MASK AIRWAY WITH A STYLET, AND STYLET

BACKGROUND OF THE INVENTION

1. Field of the Invention

The present invention relates to a medical instrument. More particularly, the present invention relates to an improved laryngeal mask airway (LMA).

2. Description of the Related Art

In the case of anesthesia and apnea patients, the top priority is the provision of pulmonary gas by emergency medical personnel. Among the various respiration sustaining instruments, the LMA, due to its ease of operability, is a common alternative to endrotracheal intubation.

Figure 1:
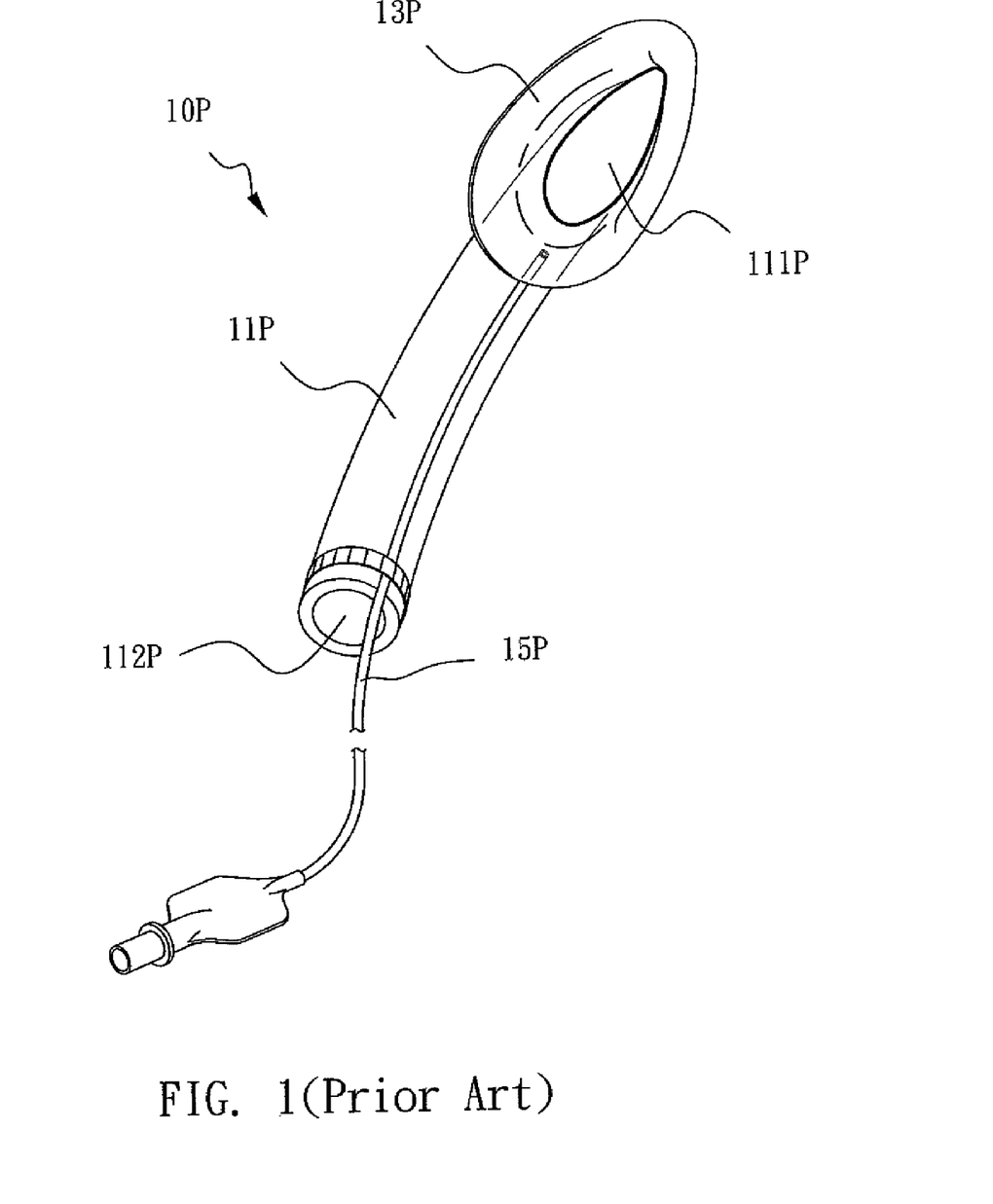
FIGS. 1 to 4 are illustrations of the LMA used in the prior art.

Please refer to FIG. 1 for the structure of a conventional LMA 10P. Basically, the LMA 10P comprises a flexible tubular portion 11P, an inflatable sealing cuff 13P, and an inflation tube 15P. The flexible tubular portion 11P comprises a first opening part 111P and a second opening part 112P. The inflatable sealing cuff 13P is disposed surrounding the first opening part 111P. The inflation tube 15P has one end connected to the inflatable sealing cuff 13P and the other end directing gas into the inflatable sealing cuff 13P.

Figure 2:
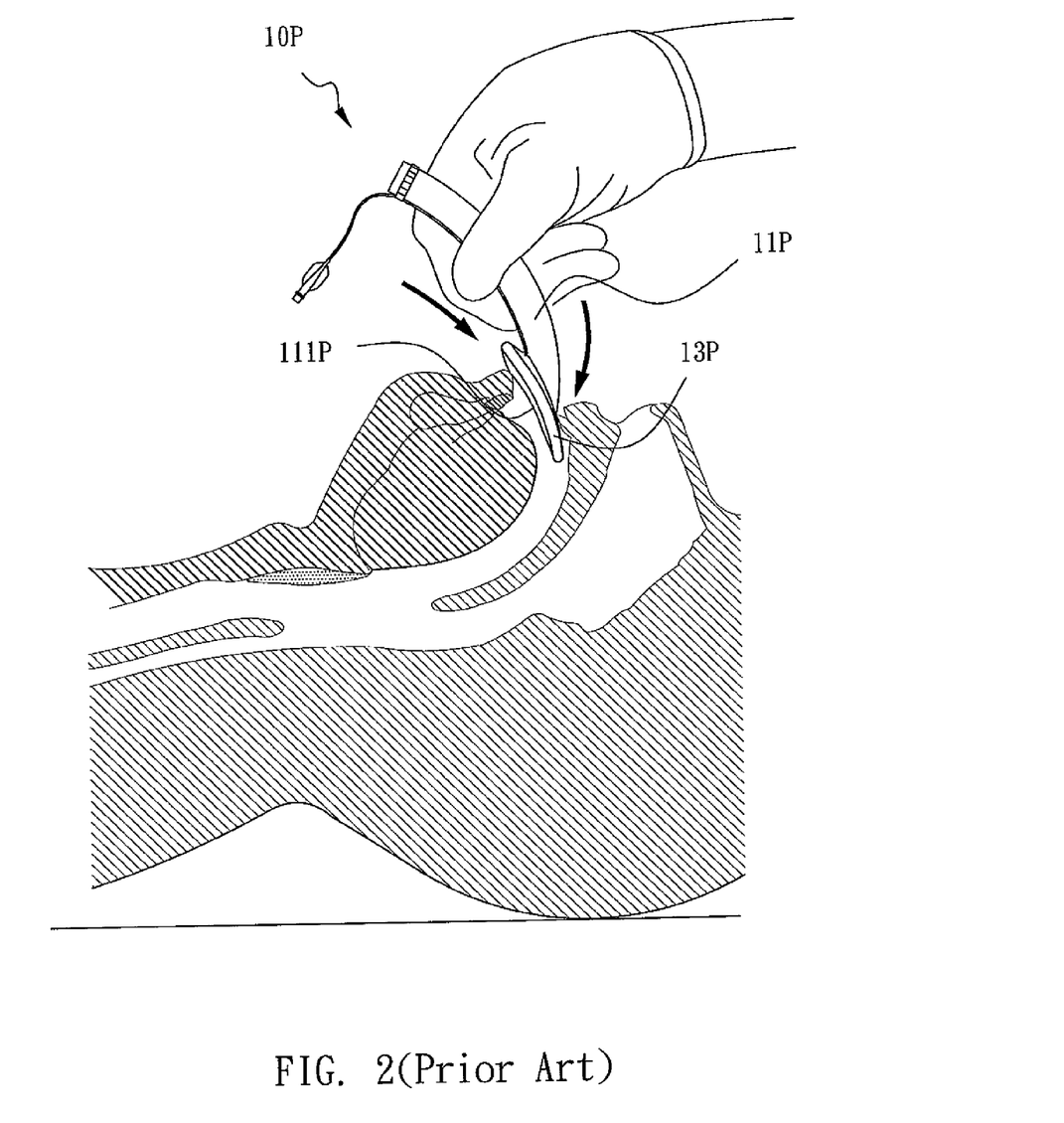
Figure 3:
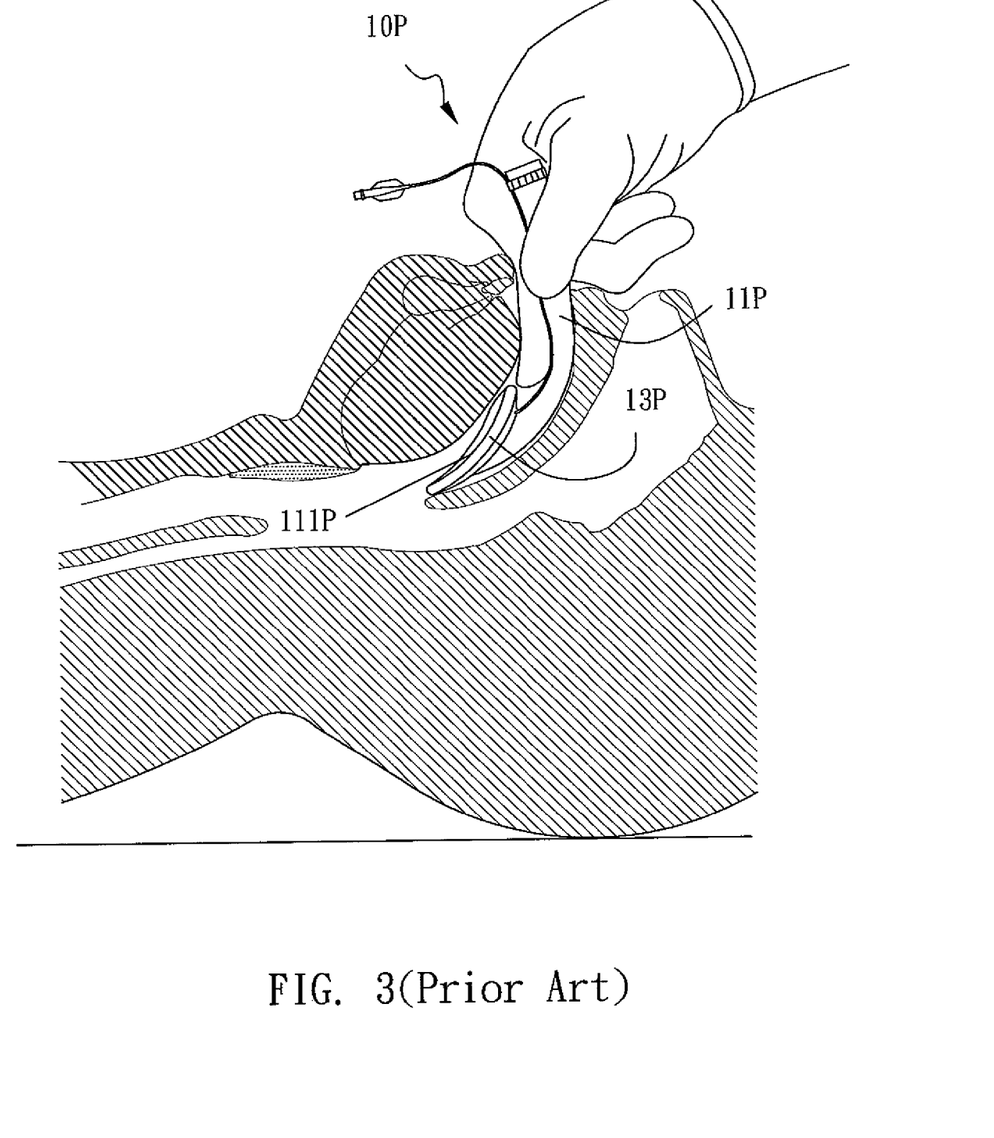
Figure 4:
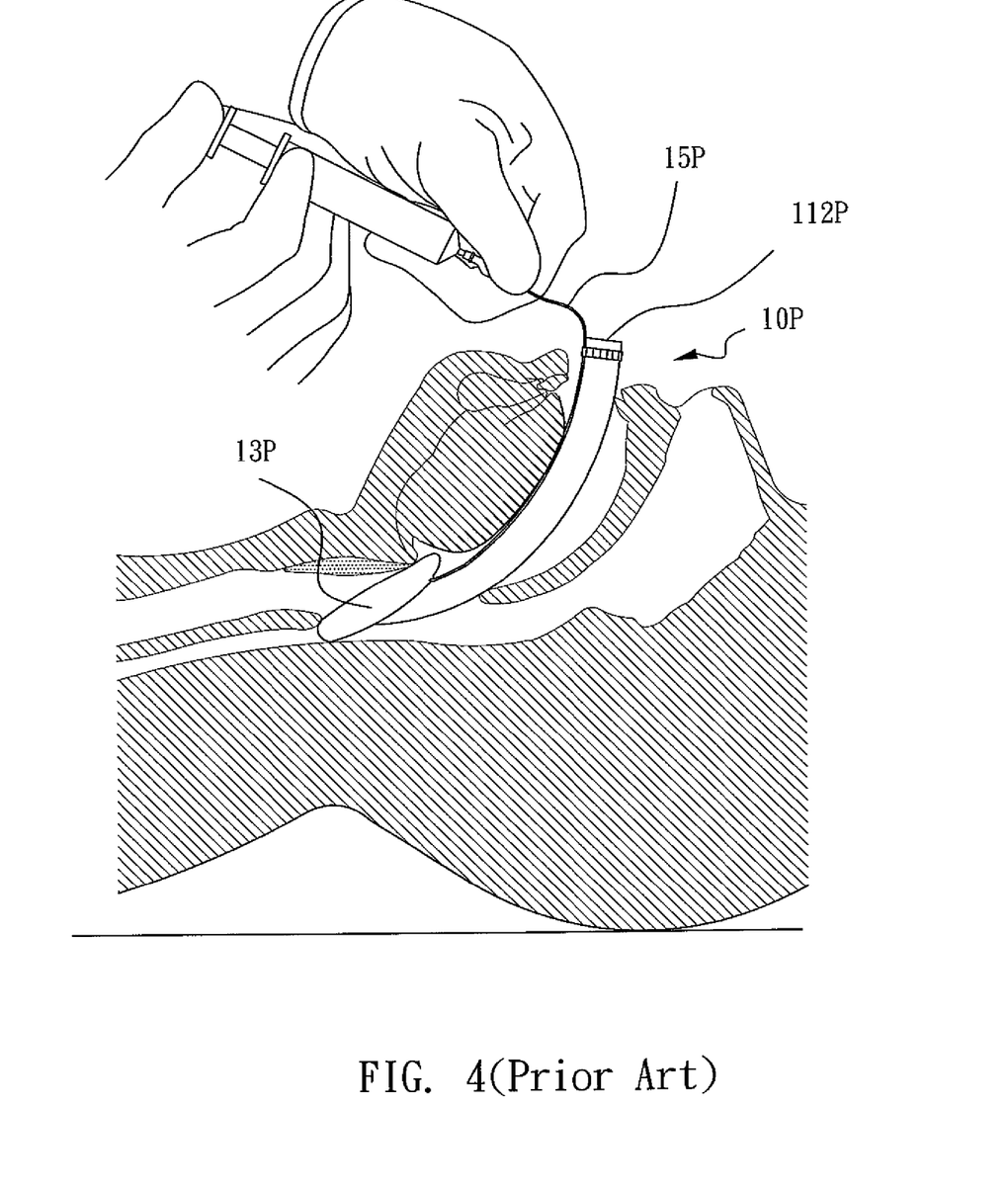

Please refer to FIGS. 2 to 4 for illustrative diagrams showing the conventional laryngeal mask 10P in use. First, a user may insert the LMA 10P into a patient's mouth by the end having the inflatable sealing cuff 13P, which is in a deflated condition. When the inflatable sealing cuff 13P reaches a deeper part of the mouth, the user will then have to insert his/her finger into the patient's mouth to bend the front end of the LMA 10P to make the structure of the LMA 10P conform with the structure of the patient's upper jaw. In addition, due to the softness of the LMA 10P, the user may not exert force thereby. Thus, the user has to push aside the tongue with his/her finger to bend the first opening part 111P and the flexible tubular portion 11P to such an extent that they can reach past the upper jaw to the opening of the trachea, as shown in FIG. 3. In FIG. 4, when the LMA 10P gets to a specific position, the user may then aerate the inflatable sealing cuff 13P from the inflation tube 15P so as to form a sealing mask in the patient's throat. The sealing mask may encompass the opening of the trachea and form an air passage thereby. After that, the user may direct gas, such as oxygen, from the second opening part 112P to maintain the patient's respiration.

Accordingly, during the installation of an LMA 10P, users always have to insert their finger(s) (especially their index fingers) into a patient's mouth to pass the soft, inconvenient LMA 10P through the upper jaw because of the obstruction of the patient's tongue. In general, this displacement by fingers may cause two problems. First, there is the risk that the user may be bitten by the patient during the installation of an LMA 10P. Second, in a case where a patient's oral space is overly small, which may be caused by an overly small mouth, an overly tight tooth joint, or an overly thick tongue, a user may encounter difficulty inserting his/her finger(s) into the patient's mouth, resulting in failure to install the LMA 10P.

In addition to the LMA 10P mentioned above, an LMA with a gastric access tube has also been disclosed in the pertinent art, such as the one disclosed in U.S. Pat. No. 5,241,956. The major function of the gastric access tube is that it that allows for easy passage of a gastric tube or can serve as an escape conduit for regurgitant fluid, thus preventing aspiration and pulmonary contamination.

SUMMARY OF THE INVENTION

It is an object of the present invention to provide a stylet usable with an LMA having a gastric access tube in order to enable users to install the LMA without having to insert their fingers into the patient's mouth.

It is another object of the present invention to provide an LMA installation kit which may be assembled by a user easily to facilitate the installation of an LMA.

It is still another object of the present invention to provide an LMA with a stylet. When the stylet in the LMA is bent by a user to a certain curvature, the stylet, which is relatively more rigid than the LMA, may keep the relatively softer LMA in the curvature and provide some rigidity to the LMA, enabling the user to exert force to the farther end of the LMA. Accordingly, the LMA with a stylet of this invention may not only facilitate the installation of the LMA into a patient's upper airway but also enable users to conduct the installation without inserting their fingers.

To achieve the aforementioned objects, this invention provides an LMA installation kit comprising: an LMA comprising a gastric access tube which comprises an inlet end and an outlet end; and a stylet capable of being inserted into the gastric access tube from the inlet end and, when bent, changing the original shape of the LMA.

In addition, this invention provides an LMA with a stylet comprising: an LMA comprising a gastric access tube; and a stylet inserted in the gastric access tube, with said stylet, when bent, being capable of changing the original shape of the LMA.

Moreover, this invention provides a stylet usable with an LMA with a gastric access tube, with the stylet comprising a substantially elongated main part capable of changing the original shape of the LMA when bent.

In some situations to ensure that the stylet will not penetrate the outlet end of the gastric access tube, the present invention provides a clasp mountable on the stylet. When the length of the stylet in the gastric access tube exceeds a predefined length, the stylet will be restrained by the clasp. The clasp may be installed adjustably so that a user may adjust the insertable length.

In some situations, the opening at the outlet end of the gastric access tube is of a specific size. More specifically, the size of the opening is large enough to permit the passage of a gastric tube for extracting regurgitant fluid while small enough to prevent the stylet from penetrating therefrom and thus harming the patient by direct contact or by causing contamination.

In addition, the stylet may be used with an image system so that a user may observe the patient's upper airway during the installation of the LMA. For example, video-recording and image-capturing functions may be obtained by the use of an image-capturing unit. The image captured by the image-capturing unit may be shown with the use of a display unit. The image captured by the image-capturing unit may be transmitted to an external display wirelessly with the use of a signal emission unit. In short, various units may be integrated with this invention whenever needed.

Furthermore, in the LMA installation kit and the LMA with a stylet, the penetration of the gastric access tube by the stylet may be prevented by different ways. For example, the clasp may be installed at the inlet end of the gastric access tube. In addition, special design features of the LMA may also have similar effects. For example, the formation of indentations close to the outlet end of the gastric access tube and modification of the opening of the gastric access tube to make it smaller are both viable solutions.

It should be noted that even though several objects are described herein, they are just enumerated as examples and not presented as a complete list. In other words, the objects of this invention are not limited thereto. Any practices of the present invention, even if not directed to fulfill the objects mentioned above, shall still fall within the scope of this invention. Meanwhile, the selection of wordings focuses on revealing the invention as simply as possible so that readers may understand the invention without extra effort. Thus, the interpretation of the wordings shall be done broadly without unnecessary limits.

Other objects, advantages, and novel features of the invention will become more apparent from the following detailed description when taken in conjunction with the accompanying drawings.

BRIEF DESCRIPTION OF THE DRAWINGS

These and other objects and advantages of the present invention will become apparent from the following description of the accompanying drawings, which disclose several embodiments of the present invention. It is to be understood that the drawings are to be used for purposes of illustration only, and not as a definition of the invention.

In the drawings, wherein similar reference numerals denote similar elements throughout the several views.

DETAILED DESCRIPTION OF THE PREFERRED EMBODIMENTS

Figure 5:
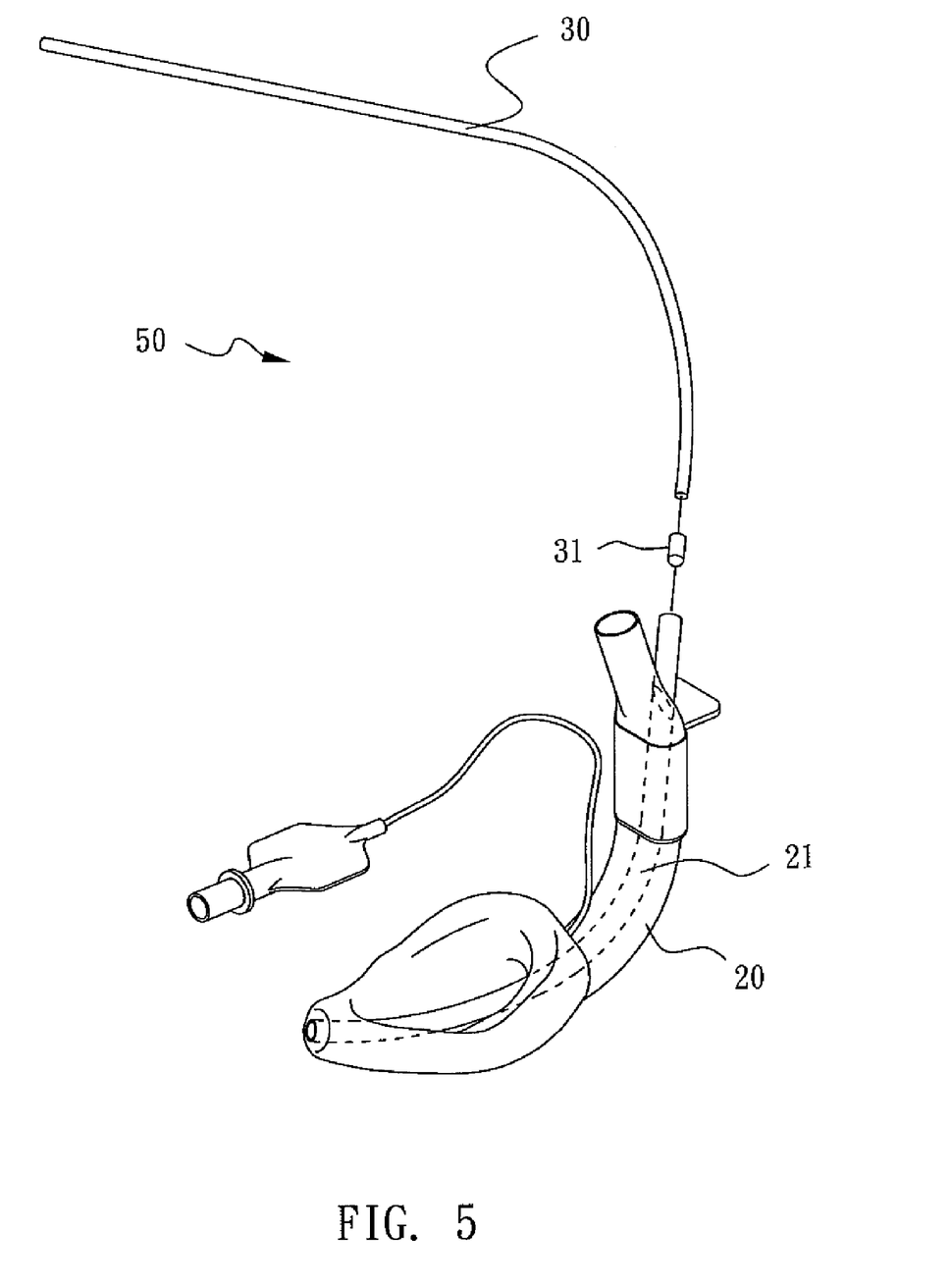
FIG. 5 is an illustration of one embodiment of the LMA installation kit of this invention.

Please refer to FIG. 5 for an illustration of one embodiment of the LMA installation kit 50 of this invention. The LMA installation kit 50 mainly comprises an LMA 20 comprising a gastric access tube 21 which comprises an inlet end and an outlet end; and a stylet 30 capable of being inserted into the gastric access tube 21 from the inlet end and, when bent, changing the original shape of the LMA 20. To prevent the stylet 30 from penetrating the gastric access tube 21 and injuring the patient, a soft cap 31, which may be made of any biocompatible material, may selectively be mounted on the stylet 30. Alternatively, the end of the stylet 30 insertable into the gastric access tube 21 may be made of soft material in some situations so as to prevent injury.

In addition, the material of the stylet 30 may be chosen from any substance that is not completely rigid so that the stylet 30 may be bent by the user to a specific curvature suitable for the installation of the LMA 20.

Figure 6:
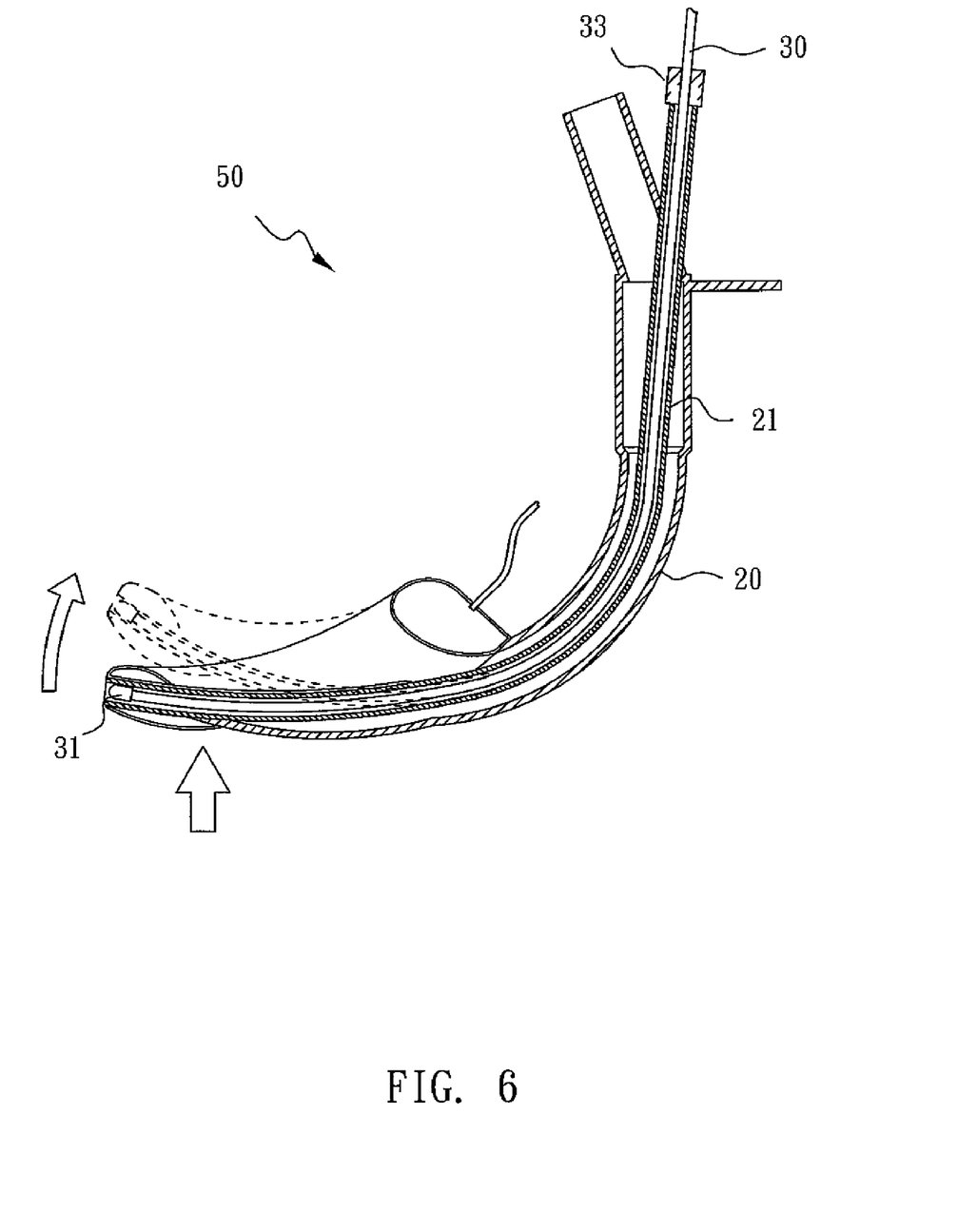
FIG. 6 is a sectional view of one embodiment of the LMA installation kit of this invention.

Refer to FIG. 6 for a sectional view of one embodiment of the LMA installation kit 50 of this invention. As shown, the stylet 30 may be inserted into the gastric access tube 21 of the LMA 20. Because the gastric access tube 21 of the LMA 20 may bear the force directed from the stylet 30, the user may use this characteristic to change the curvature of the LMA 20 when the stylet 30 is inserted into the gastric access tube 21 and bent. Thus, the present invention allows users to assemble the LMA installation kit 50 and to bend the stylet 30 to a desirable curvature in light of the physical characteristics of a patient so as to facilitate the installation of the LMA 20.

To prevent users from penetrating the gastric access tube 21 with the stylet 30 and thus contaminating the patient's upper airway, the LMA installation kit 50 of this invention may selectively contain a clasp 33 mountable on the stylet 30 for controlling the length of the stylet 30 insertable into the gastric access tube 21. In certain situations, the clasp member 33 is adjustably installed. Therefore, users may adjust the length of the stylet 30 insertable into the gastric access tube 21 according to existing conditions.

Figure 7:
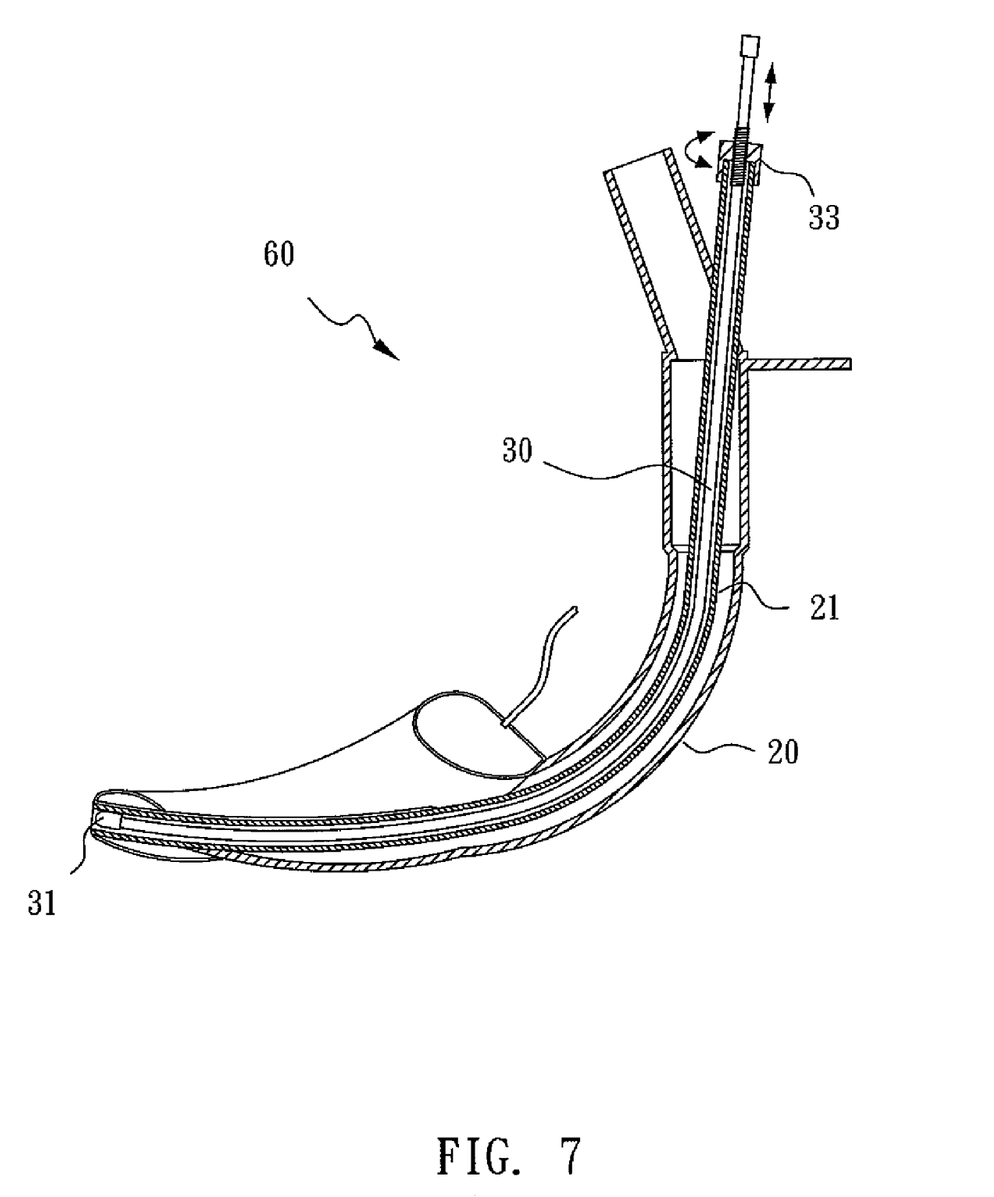
FIG. 7 is an illustration of one embodiment of the LMA with a stylet of this invention.

Refer to FIG. 7 for an illustration of one embodiment of the LMA with a stylet 60 of this invention. The LMA with a stylet 60 mainly comprises: an LMA 20 which comprises a gastric access tube 21; and a stylet 30 inserted into the gastric access tube 21. Said stylet 30, when bent, is capable of changing the original shape of the LMA 20.

Similarly, to prevent users from penetrating the gastric access tube 21 with the stylet 30 and thus contaminating the patient's upper airway, the LMA with a stylet 60 of this invention may selectively contain a clasp 33 mountable on the stylet 30 for controlling the length of the stylet 30 insertable into the gastric access tube 21. In certain situations, the clasp member 33 is adjustably installed. Therefore, users may adjust the length of the stylet 30 insertable into the gastric access tube 21 according to need. As shown in FIG. 7, corresponding threads complementary to that of the stylet 30 may be formed on the clasp 33, enabling users to move the stylet 30 back or forth by rotation.

Figure 8:
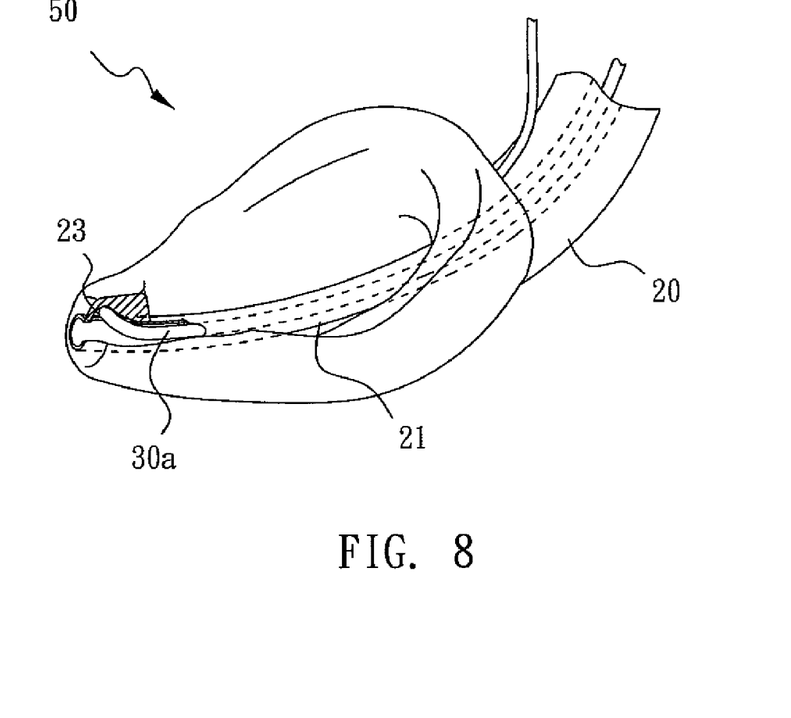
FIGS. 8 to 11 are illustrations of different embodiments of the LMA installation kit of this invention.

Undoubtedly, different designs may be applied to the stylet, LMA, or gastric access tube to keep the stylet from penetrating the gastric access tube. Please refer to FIGS. 8 to 11 for illustrations of different embodiments of the LMA installation kit 50 of this invention. In FIG. 8, an indentation 23 capable of restraining the stylet 30a may be formed adjacent to the opening of the gastric access tube 21 of the LMA 20. In that case, the stylet 30a will be kept in position when the front end of the stylet 30a enters the indentation 23, effectively preventing the stylet 30a from causing any contamination or injury. In addition, different designs may be applied to the stylet 30b so that it may be directed into the indentation 23 more easily.

Figure 9:
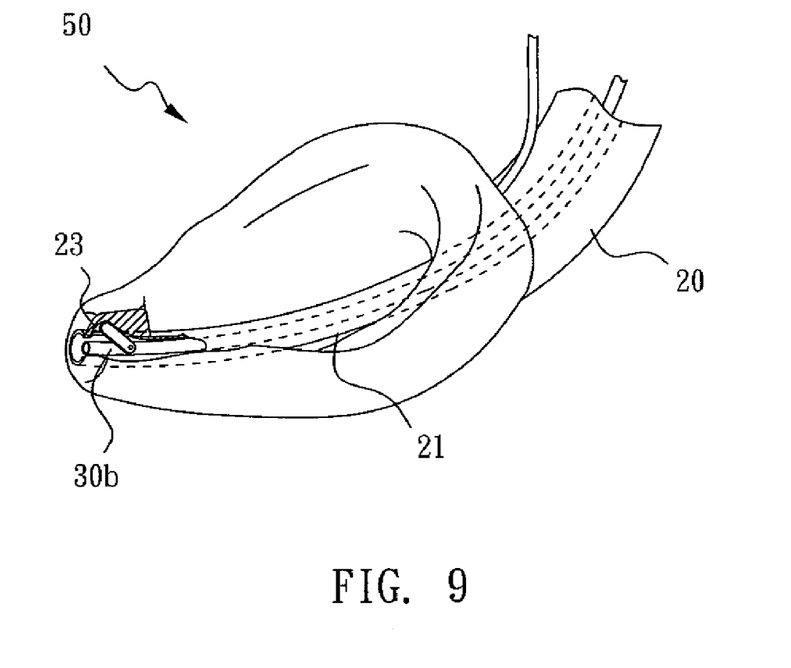
Figure 10:
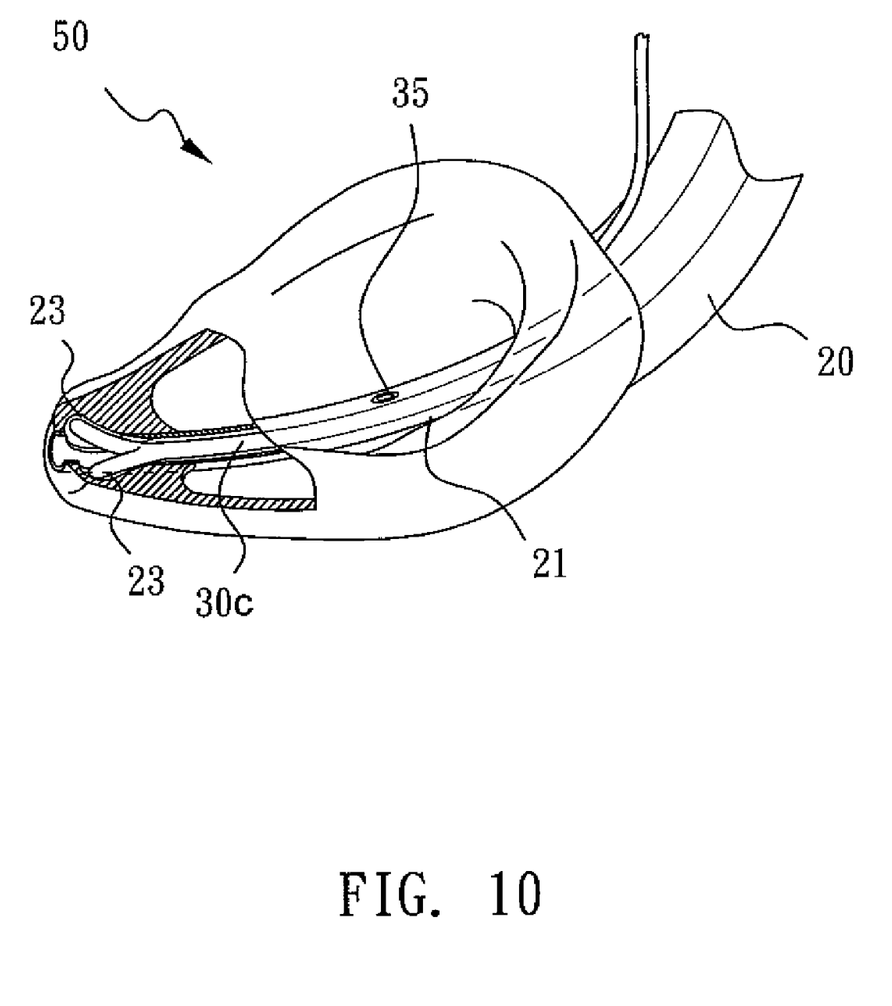

In FIG. 9, the stylet 30b has a fork structure which can be easily fitted into the indentation 23 to prevent the stylet 30b from penetrating the gastric access tube 21. Similarly, as shown in FIG. 10, two indentations 23 are formed close to the opening of the gastric access tube 21 of the LMA 20. The design shown in FIG. 10 is especially suitable for a stylet 30c with another fork structure. In addition, the LMA 20 of this invention may be selectively made of transparent material so as to allow the stylet 30c, which has an image-capturing unit 35, to capture images. It should be noted that, due to the high costs of the transparent material, the use of the transparent material in the LMA 20 may be limited only to the area around the image-capturing unit 35. Also, the image-capturing unit 35 is not limited to use with only one certain type of stylet 30, but various types of stylet 30 are applicable.

Figure 11:
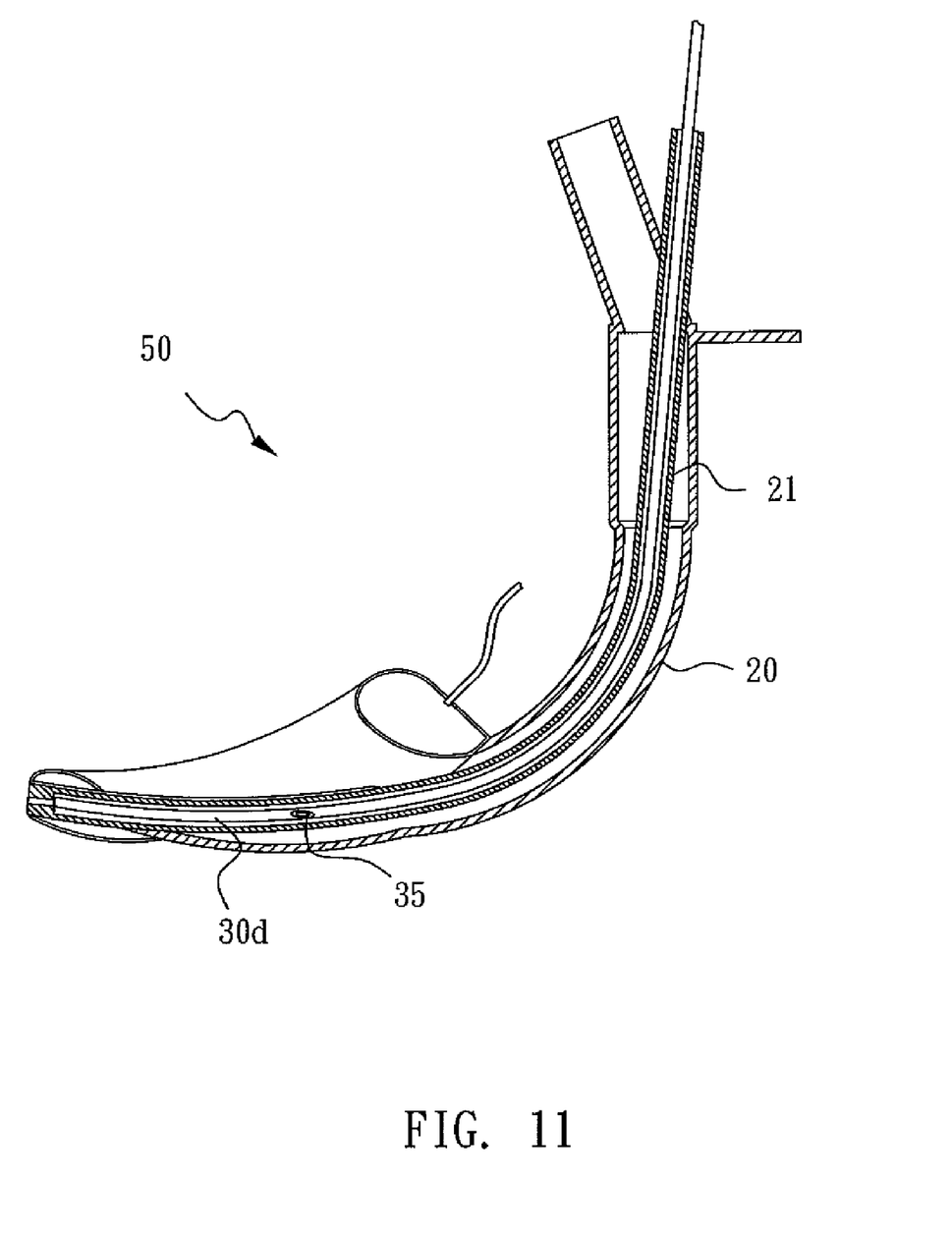

In FIG. 11, a gastric access tube 21 with a smaller opening is used to restrain the stylet 30d from penetrating the gastric access tube 21. In this case, the size of the opening is large enough to permit the passage of a gastric tube for extracting the regurgitant fluid while small enough to prevent the stylet 30*d* from protruding therefrom and thus harming the patient by direct contact or causing contamination.

Figure 12:
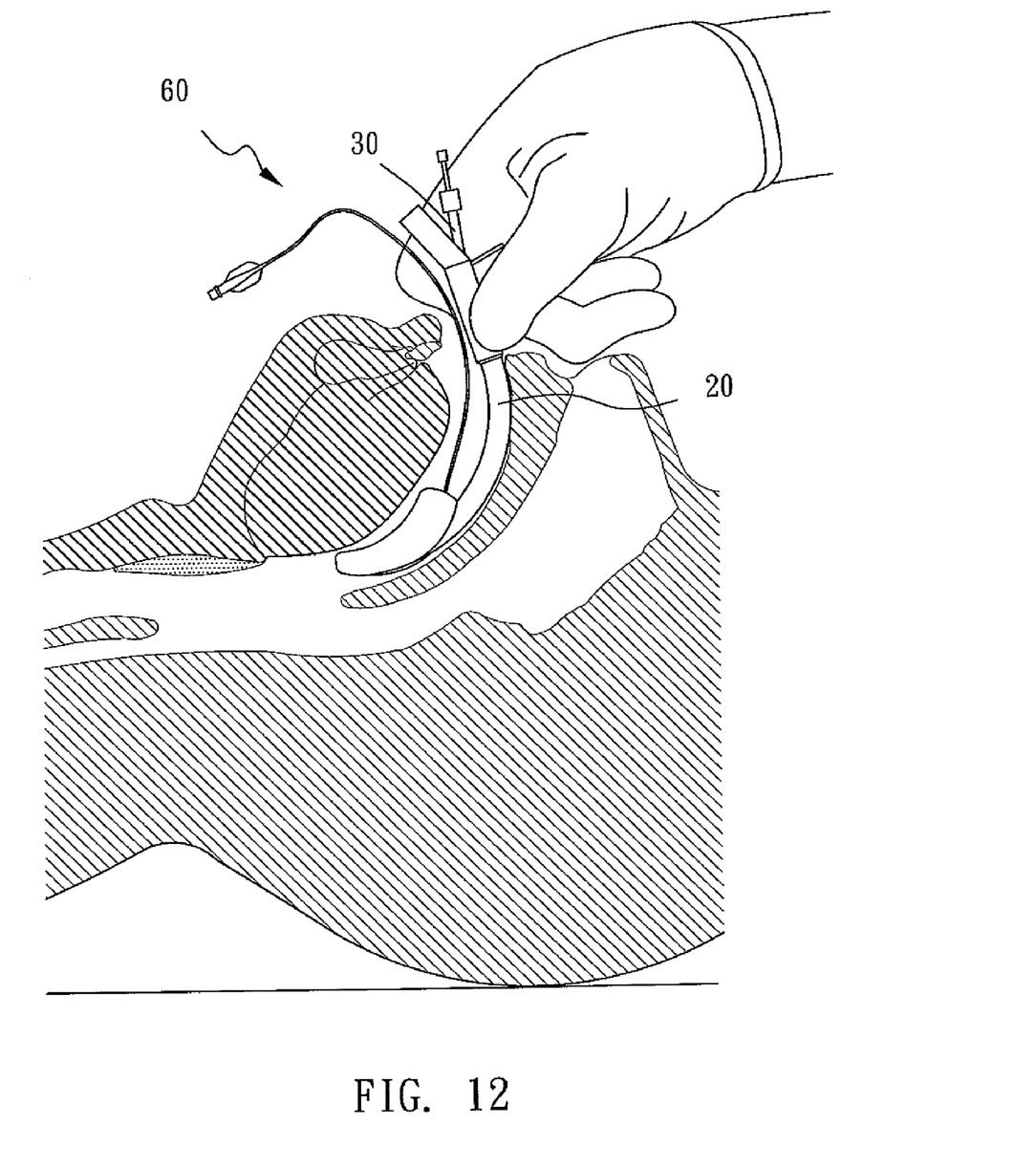
FIG. 12 is an illustration of one embodiment of the LMA with a stylet of this invention in use.

Please refer to FIG. 12 for an illustration of one embodiment of the LMA with a stylet 60 of this invention in use. Before being applied to a patient, the LMA with a stylet 60 is bent in advance to a specific curvature. Therefore, a user may easily pass the LMA 20 through the patient's upper jaw without having to insert a finger into the patient's mouth to bend the LMA 20. Then, the LMA 20 may resume its original shape after the user withdraws the stylet 30. The installation may be completed 20 by the inflation of the LMA 20.

Figure 13:
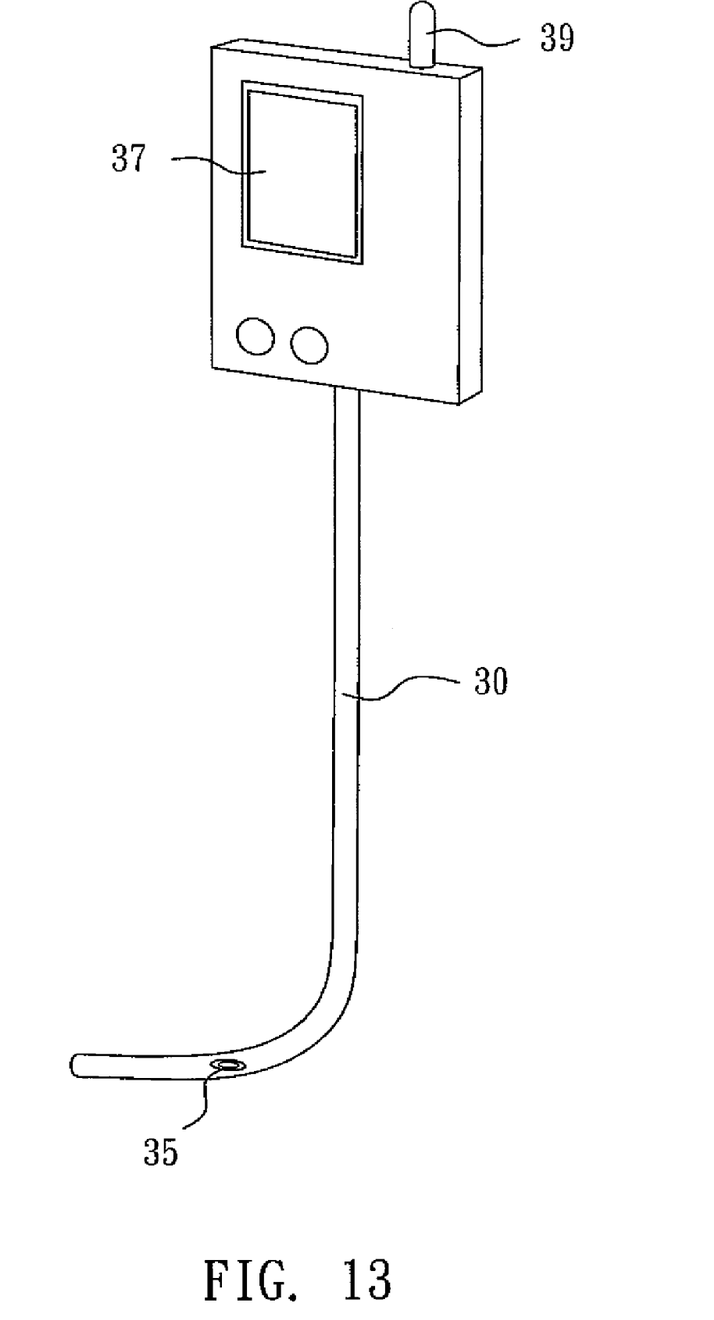
FIG. 13 is an illustration of one embodiment of the stylet of this invention.

Finally, refer to FIG. 13 for an illustration of one embodiment of the stylet 30 of this invention. As shown, the stylet 30 comprises an image-capturing unit 35 for capturing an image from a patient's upper airway. The image may then be directly shown on a display unit 37 installed at one end of the stylet 30, enabling a user to determine the position of the LMA 20 in the upper airway. In addition, a signal emission unit 39 may be selectively used to wirelessly transmit the image captured by the image-capturing unit 35 to an external display. However, it should be noted that each unit mentioned above may be applied to the stylet 30 either individually or collectively.

Accordingly, the stylet 30 of the present invention, when used in an LMA 20, may not only facilitate the installation of the LMA 20 but may also provide a precise condition assessment capability by enabling users to observe the installation process.

Although the present invention has been explained in relation to its preferred embodiments, it is to be understood that many other possible modifications and variations can be made without departing from the spirit and scope of the invention as hereinafter claimed.

What is claimed is:

1. A laryngeal mask airway installation kit comprising:
   a laryngeal mask airway comprising a gastric access tube including an inlet end and an outlet and wherein the laryngeal mask airway further comprises an indentation, the indentation preventing the stylet from passing through the outlet end of the gastric access tube,
   a stylet inserted into the gastric access tube from the inlet end and, wherein a front end of the stylet wherein the front end of the stylet is a fork structure, insertable into the inlet end of the gastric access tube is made of soft material softer than a portion of the stylet changing the original shape of the laryngeal mask airway.

2. The laryngeal mask airway installation kit as claimed in claim 1, wherein the stylet comprises a soft cap mounted on the front end insertable into the gastric access tube.

3. The laryngeal mask airway installation kit as claimed in claim 2, further comprising a clasp mountable to the stylet for controlling the length of the stylet insertable into the gastric access tube.

4. The laryngeal mask airway installation kit as claimed in claim 1, wherein the movement of the stylet in the gastric access tube is limited, this limitation preventing penetrating of the gastric access tube.

5. A laryngeal mask airway installation kit comprising:
   a laryngeal mask airway comprising a gastric access tube including an inlet end and an outlet end, wherein the laryngeal mask airway further comprises an indentation formed in the gastric access tube spaced from the outlet end; and
   a stylet inserted into the gastric access tube from the inlet end and, the stylet having a front end, wherein the front end of the stylet is a fork structure, with the front end entering the indentation preventing the stylet from passing through the outlet end of the gastric access tube.

6. The laryngeal mask airway installation kit as claimed in claim 5, wherein the stylet further comprises an image-capturing unit for capturing an image.

7. The laryngeal mask airway installation kit as claimed in claim 6, wherein the stylet further comprises a display unit electrically connected to the image-capturing unit for displaying the image captured by the image-capturing unit.

8. The laryngeal mask airway installation kit as claimed in claim 6, wherein the stylet further comprises a signal emission unit electrically connected to the image-capturing unit for wirelessly transmitting the image captured by the image-capturing unit to an external display.

9. The laryngeal mask airway installation kit as claimed in claim 5 further comprising another indentation formed in the gastric access tube spaced from the outlet end and diametrically opposite the indentation.

\* \* \* \* \*